United States Patent [19]
Carlin

[11] Patent Number: 5,888,479
[45] Date of Patent: Mar. 30, 1999

[54] METHOD FOR DETERRING SMOKING

[76] Inventor: Edward J. Carlin, 794 5$^{th}$ St., Secaucus, N.J. 07094

[21] Appl. No.: 2,131

[22] Filed: Dec. 31, 1997

[51] Int. Cl.$^6$ ............................. A61K 7/16; A61K 33/24; A61K 33/30; A61K 33/34
[52] U.S. Cl. ........................... 424/49; 131/270; 131/359; 514/343; 514/813; 514/922; 424/604; 424/630; 424/641; 424/650; 414/653
[58] Field of Search ................................ 424/49–58, 604, 424/630, 641, 650, 653; 514/813, 922, 343; 131/270, 359

[56] References Cited

U.S. PATENT DOCUMENTS

| | | | |
|---|---|---|---|
| 3,572,348 | 3/1971 | Morman et al. | 131/7 |
| 3,655,868 | 4/1972 | Vagenius et al. | |
| 4,055,191 | 10/1977 | Morman et al. | 131/9 |
| 4,235,251 | 11/1980 | Bryant et al. | 131/140 B |
| 4,257,430 | 3/1981 | Collins et al. | 131/140 B |
| 4,835,162 | 5/1989 | Abood . | |
| 4,980,172 | 12/1990 | Fey . | |
| 5,032,612 | 7/1991 | Smolko et al. | |
| 5,037,634 | 8/1991 | Williams et al. | |
| 5,211,940 | 5/1993 | Ishiguro et al. | |
| 5,286,479 | 2/1994 | Garlich et al. | |
| 5,628,986 | 5/1997 | Sanker et al. | |

FOREIGN PATENT DOCUMENTS 1097075  12/1967  United Kingdom .

OTHER PUBLICATIONS

Hymowitz et al Preventive Medicine 25(5):537–546 Sep.–Oct. 1996 "Effects of a 2.5MG Silver Acetate Lozenge on Initial and Long–Term Smoking Cessation".

Tso et al Plant Physiol 51(4):805–806 (1973) "Effects of Some Rare Elements on Nicotine Content of the Tobacco Plant".

*Primary Examiner*—Shep K. Rose
*Attorney, Agent, or Firm*—Arthur Jacob

[57] ABSTRACT

A method for reducing the desire of a person to smoke tobacco includes orally administering to the person an aqueous solution containing a polyvalent cation derived from a metal selected from the group consisting of palladium, copper, zinc, aluminum, tin, and bismuth. The method includes smoking tobacco by the person to whom the solution is administered, subsequent to the oral administration of the solution.

9 Claims, No Drawings

METHOD FOR DETERRING SMOKING

The present invention relates generally to assisting smokers of tobacco in deterring smoking and pertains, more specifically, to reducing the desire to smoke by orally administering aqueous solutions containing polyvalent cations of selected metals.

Among the very large number of cigarette smokers in the United States alone, there are many who wish to reduce or altogether discontinue the consumption of cigarettes, but are unable to do so readily because of a developed physical or psychological dependence on cigarettes. Recent revelations concerning the effects of cigarette smoking on a smoker's health have given increased impetus to some smokers toward reducing or discontinuing the practice, with the result that a variety of smoking deterrents have been offered in an effort to assist smokers in accomplishing their goal. However, many products currently being promoted as smoking deterrents have been found to exhibit significant drawbacks.

As documented in the Federal Register, Volume 47, No. 2, at page 492, many purported smoking deterrents are merely strong flavors, such as capsicum, ginger, eucalyptus oil and the like, or topical anesthetics, such as clove, menthol, benzocaine and the like, which, in addition to changing the taste of a cigarette, also will contaminate or significantly alter the perceived taste of any other ingested product. Even in the absence of eating or drinking when using these materials, the consumer essentially merely is exchanging the condition of tasting and smelling of tobacco smoke for the condition of continually tasting and smelling of some herbaceous material.

Lobelia alkaloids and pharmaceutical equivalents thereof have been used as smoking deterrents, and have been found to cause unwanted and potentially dangerous respiratory stimulation, as well as euphoric effects. Smoking of lobelia alkaloids has been found to produce sufficient psychoactive effects to be regarded as a marijuana substitute.

The use of the nitrate or acetate of silver as a smoking deterrent raises the risk of developing a non-reversible blue-black tinting of the skin, clinically known as argyria. Additionally, the tendency of silver salts to form insoluble complexes with many materials limits the manner in which compounds containing silver salts may be formulated, and restricts the properties of the finished product.

A more recently approved treatment for assisting in the reduction or discontinuance of smoking is the administration of nicotine, either orally or via transdermal delivery systems. It has been suggested that nicotine is the physically addictive component of tobacco and hence the administration of nicotine will satisfy the desire to smoke tobacco without actually smoking. However, nicotine itself is highly toxic and acts relatively rapidly to exhibit curare-like symptoms; therefore, therapeutic doses of nicotine must be very carefully controlled and given with specific, strict instructions.

The present invention avoids the shortcomings and limitations encountered in the use of products and treatments outlined above and attains several objects and advantages, some of which are summarized as follows: Provides a method for reducing the desire of a person to smoke tobacco without reliance upon currently available taste-masking techniques and all of the inherent drawbacks of such techniques; enables a smoker to deter smoking tobacco safely and effectively, and without exposure to deleterious side effects; provides a smoker with a simplified and relatively inexpensive yet effective method for reducing the desire to smoke; enables a smoker to deter smoking with increased ease and convenience; provides a method for deterring smoking, which method is amenable to widespread use, making the method available to a very large audience for adoption with minimal effort.

The above objects and advantages, as well as further objects and advantages, are attained by the present invention which may be described briefly as a method for reducing the desire of a person to smoke tobacco, the method comprising: orally administering to the person an aqueous solution containing a polyvalent cation derived from a metal selected from the group consisting of palladium, copper, zinc, aluminum, tin, and bismuth. Further, the method includes smoking tobacco by the person to whom the solution is administered, subsequent to the oral administration of the solution.

The invention will be understood more fully, while still further objects and advantages will become apparent, in the following detailed description of preferred embodiments of the invention.

In accordance with the present invention, an aqueous solution of polyvalent cations derived from one or more of the following metals:

| | | |
|---|---|---|
| Palladium | Zinc | Tin |
| Copper | Aluminum | Bismuth | is introduced into the mouth of a smoker. Preferably, the aqueous solution contains about 0.005 to 5.0 percent by weight of a salt or a mixture of salts of the selected metal or metals. For some time subsequent to the introduction of the aqueous solution, upon smoking by the person to whom the aqueous solution is administered, the taste of tobacco smoke, and more particularly, cigarette smoke, is significantly altered in a manner serving to deter the desire of the person to whom the aqueous solution is administered to continue smoking. The solution preferably includes flavoring ingredients for increasing palatability, and is delivered in any one of a variety of forms, the preferred form being either a mouthwash or a spray. All that is necessary is to expose the mouth of the human smoker to the aqueous solution of the invention, and the taste of cigarette smoke is rendered undesirable enough for a sufficient duration to discourage smoking and thereby assist the smoker in reducing or entirely discontinuing smoking.

The following are illustrative examples of aqueous solutions formulated in accordance with the invention and administered orally by rinsing with twenty milliliters of solution for thirty seconds. All of the solutions in the following examples included 4% ethyl alcohol, 0.9% poloxamer 407, 0.9% polysorbate 20, about 0.38 to 0.68% flavoring ingredients, and 50% glycerin, all by weight, with the balance being distilled water.

EXAMPLE 1

An aqueous solution containing 0.25% copper gluconate was found to be effective at one and one-half hours after oral administration.

EXAMPLE 2

An aqueous solution containing 0.35% copper gluconate was found to be effective at one, two, three, and four hours, and overnight, after oral administration.

EXAMPLE 3

An aqueous solution containing 0.20% palladium chloride was found to be effective at one hour after oral administration.

EXAMPLE 4

An aqueous solution containing 0.20% zinc gluconate was found to be effective at one hour after oral administration.

EXAMPLE 5

An aqueous solution containing 0.20% aluminum chloride was found to be effective at one hour after oral administration.

EXAMPLE 6

An aqueous solution containing 0.20% stannic chloride was found to be effective at one hour after oral administration.

EXAMPLE 7

An aqueous solution containing 0.20% bismuth chloride was found to be effective at one hour after oral administration.

It will be apparent that the present invention attains the several objects and advantages summarized above, namely: Provides a method for reducing the desire of a person to smoke tobacco without reliance upon currently available taste-masking techniques and all of the inherent drawbacks of such techniques; enables a smoker to deter smoking tobacco safely and effectively, and without exposure to deleterious side effects; provides a smoker with a simplified and relatively inexpensive yet effective method for reducing the desire to smoke; enables a smoker to deter smoking with increased ease and convenience; provides a method for deterring smoking, which method is amenable to widespread use, making the method available to a very large audience for adoption with minimal effort.

It is to be understood that the above detailed description of preferred embodiments of the invention is provided by way of example only. Various details of procedure may be modified without departing from the true spirit and scope of the invention, as set forth in the appended claims.

The embodiments of the invention in which an exclusive property or privilege is claimed are defined as follows:

1. A method for reducing the desire of a person to smoke tobacco, the person being a smoker of tobacco, desiring to reduce the desire to smoke, the method comprising: orally administering to the person an aqueous solution containing a polyvalent cation derived from a metal selected from the group consisting of palladium, copper, zinc, aluminum, tin, and bismuth.

2. The method of claim 1 wherein the aqueous solution contains about 0.005 to 5.0 percent by weight of a salt of the selected metal.

3. The method of claim 2 wherein the aqueous solution contains flavor.

4. The method of claim 3 wherein the aqueous solution is a mouthwash.

5. A method for reducing the desire of a person to smoke tobacco, the person being a smoker of tobacco, desiring to reduce the desire to smoke, the method comprising: orally administering to the person an aqueous solution containing a mixture of polyvalent cations derived from metals selected from the group consisting of palladium, copper, zinc, aluminum, tin, and bismuth.

6. The method of claim 5 wherein the solution contains about 0.005 to 5.0 percent by weight of a mixture of salts of the selected metals.

7. The method of claim 6 wherein the aqueous solution contains flavor.

8. The method of claim 7 wherein the solution is a mouthwash.

9. The method of any one of claims 1 through 8 including smoking tobacco by the person to whom the solution is administered, subsequent to the oral administration of the solution.

* * * * *